United States Patent
Boutos

(10) Patent No.: US 6,675,052 B2
(45) Date of Patent: Jan. 6, 2004

(54) ELECTRODE APPARATUS FOR STIMULATING PENILE TISSUE

(76) Inventor: David Boutos, 4950 Mountain Creek Dr., Las Vegas, NV (US) 89148

( * ) Notice: Subject to any disclaimer, the term of this patent is extended or adjusted under 35 U.S.C. 154(b) by 489 days.

(21) Appl. No.: 09/774,409

(22) Filed: Jan. 31, 2001

(65) Prior Publication Data

US 2003/0130715 A1 Jul. 10, 2003

(51) Int. Cl.[7] .................................................. A61N 1/04
(52) U.S. Cl. .......................................... 607/143; 607/39
(58) Field of Search ............................... 607/115, 138, 607/143, 148, 149, 39; 600/382, 384, 386; 606/41

(56) References Cited

U.S. PATENT DOCUMENTS

| | | | |
|---|---|---|---|
| 5,571,118 A | 11/1996 | Boutos | 607/138 |
| 5,697,966 A | 12/1997 | Boutos | 607/138 |
| 5,782,902 A | 7/1998 | Boutos | 607/143 |
| 6,151,527 A | * 11/2000 | Boutos | 607/138 |
| 6,246,915 B1 | * 6/2001 | Boutos | 607/143 |

* cited by examiner

*Primary Examiner*—Jeffrey R. Jastrzab
(74) *Attorney, Agent, or Firm*—Jordan M. Meschkow; Lowell W. Gresham; Meschkow & Gresham PLC

(57) ABSTRACT

Electrodes for stimulating penile tissue are shown. Electrical stimulation to such areas is intended to induce excitation and orgasm in males, particularly where impotence is a problem. Four embodiments of an electrode apparatus include a flexible ring (22) and an electrically conductive section (24) having a first end (26) coupled to and extending from the flexible ring (22), and an intermediate portion (30) extending through a hole (32) in the flexible ring (22). An electrical contact (34), in electrical communication with a second end (28) of the electrically conductive section (24), allows the section (24) to be connected to an electrical source. Auxiliary members such as conductive spheres (72, 78, 90, and 92) and additional conductive sections (86, 100) are added to the electrode apparatuses to impart specific stimuli in specific regions of the user's anatomy.

20 Claims, 4 Drawing Sheets

ELECTRODE APPARATUS FOR STIMULATING PENILE TISSUE

TECHNICAL FIELD OF THE INVENTION

The present invention relates to devices for applying electrical energy to living tissue. More particularly, the present invention relates to an apparatus for electrically stimulating penile tissue.

BACKGROUND OF THE INVENTION

It is known that medical disorders such as diabetes, leukemia, anemia, X-ray exposure, and so forth can cause impotence in males. Furthermore, it is known that the application of electrical stimulation to penile tissue can cause erection where impotence may exist due to these physiological conditions or due to psychological conditions. Indeed, it is known that the application of electrical stimulation to penile and urethral tissue can induce orgasm, even where the subject has suffered damage to the nerves serving the sex organs.

The art is replete with various devices used to apply electrical stimulation to the subject areas. Rigid rings capable of transmitting low levels of electricity to the skin and muscles are typically applied about the penis and/or the scrotum. Insertable rolled or plug-type electrodes, made to be rolled to size, or sized in a variety of sizes to fit the user's anatomy, are known for the purpose of applying low levels of electricity to the skin and muscles inside and surrounding the penis.

Rigid rings are useable for males where the application of electrical current to only a portion of penile tissue is sufficient to induce erection. However, due to the tremendously varying size of the penile tissue from rest to engorgement, the rigid ring may cause discomfort or pain to the user when the penis is engorged. In order to avoid this problem, the user may use a large diameter ring on a small diameter penis or change rings at some point prior to engorgement. Unfortunately, a rigid ring that is too large may not produce the desired affect and changing rings may be viewed as being too inconvenient.

In males, the glans, or head of the penis, is highly sensitive to stimulation. Likewise, the corona, i.e., the ridge of flesh demarcating where the glans and the shaft of the penis join, is highly sensitive. Rigid rings that are typically worn along the shaft of the penis do not provide sufficient stimulation about the glans and the corona.

Internally worn insertable electrodes are desirable to stimulate and to induce orgasm. However, many of these prior art insertable electrodes are difficult to retain in the appropriate position, uncomfortable for prolonged wear due to rigid components, and hard to effectively clean.

It would be highly advantageous, therefore, to remedy the foregoing and other deficiencies inherent in the prior art.

SUMMARY OF THE INVENTION

Accordingly, it is an advantage of the present invention to provide improvements in electrical stimulation apparatus for men.

Another object of the invention is to provide improved means for the application of electrical stimulation to the penile glans, corona, and urethral tissue.

Yet another object of the invention is to provide male stimulation apparatus that can induce erection and orgasm.

Yet another object of the invention is to provide means for the application of electrical stimulation to the penile tissue that is comfortable to wear during penile engorgement.

The above and other advantages of the present invention are carried out in one form by an electrode apparatus that includes a flexible ring and an electrically conductive section. The electrically conductive section has a first end, a second end, and an intermediate portion between the first and second ends. The first end is coupled to and extends from the flexible ring, and the intermediate portion extends through a hole in the flexible ring. An electrical contact is in electrical communication with the second end.

The above and other advantages of the present invention are carried out in another form by an electrode apparatus that includes a flexible ring and an electrically conductive section. The electrically conductive section has a first end, a second end, and an intermediate portion between the first and second ends. The first end is coupled to and extends from the flexible ring, and the intermediate portion extends through a hole in the flexible ring. The hole is sized to allow the intermediate portion of the electrically conductive section to slide within the hole. An electrically conductive sphere is coupled to and in electrical communication with the electrically conductive section in a region of the section between the first end and the intermediate portion. An electrical contact is in electrical communication with the second end.

The above and other advantages of the present invention are carried out in yet another form by an electrode apparatus that includes a flexible ring and a first electrically conductive section. The first electrically conductive section has a first end, a second end, and an intermediate portion between the first and second ends. The first end is coupled to and extends from the flexible ring, and the intermediate portion extends through a hole in the flexible ring. The hole is sized to allow the intermediate portion of the electrically conductive section to slide within the hole. An electrical contact is in electrical communication with the second end. A second electrically conductive section extends from the first electrically conductive section in a region of the first section between the first end and the intermediate portion. The second section is in electrical communication with the first section.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF THE PREFERRED EMBODIMENTS

Figure 1:
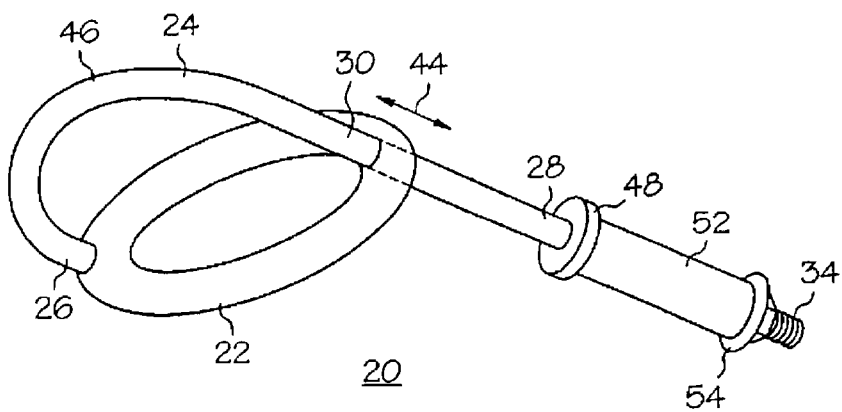
FIG. 1 shows a perspective view of an electrode apparatus in accordance with the present invention.
Figure 2:
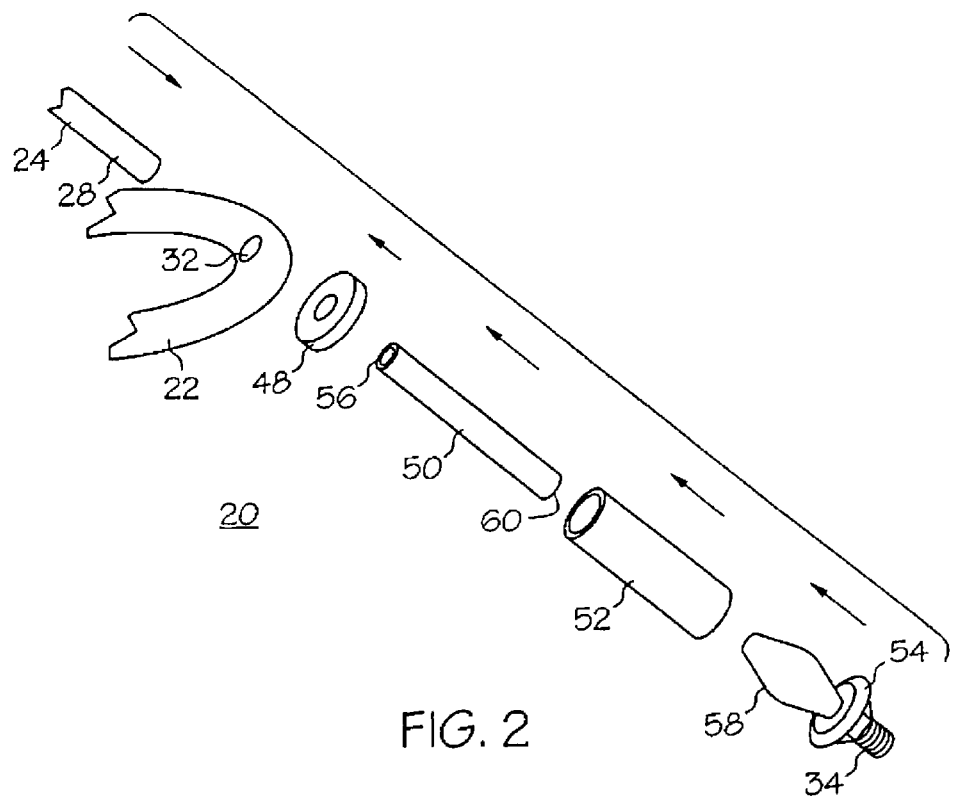
FIG. 2 shows an exploded perspective view of a portion of the electrode apparatus shown in FIG. 1.
Figure 3:
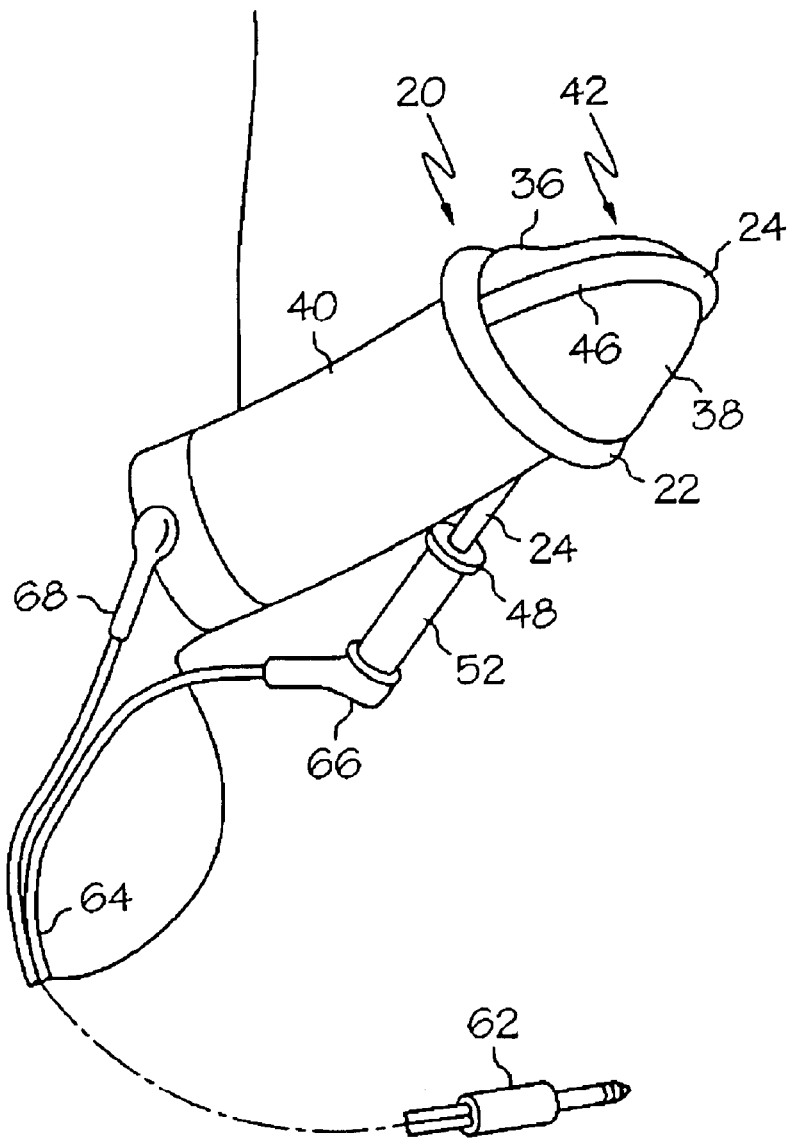
FIG. 3 shows the electrode apparatus of FIG. 1 in use.

Turning now to the drawings in which like reference characters indicate corresponding elements throughout the several views, attention is first directed to FIGS. 1–3 where an electrode apparatus 20 is shown. FIG. 1 shows a perspective view of electrode apparatus 20 in accordance with the present invention. FIG. 2 shows an exploded perspective view of a portion of electrode apparatus 20. FIG. 3 shows electrode apparatus 20 in use.

Electrode apparatus 20 includes a flexible ring 22 and an electrically conductive section 24. Electrically conductive section 24 has a first end 26, a second end 28, and an intermediate portion 30 between first and second ends 26 and 28, respectively. First end 26 is coupled to and extends from flexible ring 22 and intermediate portion 30 extends through a hole 32 extending through flexible ring 22. An electrical contact 34 is in electrical communication with second end 28.

Flexible ring 22 is fabricated from an elastomeric material such as silicone, fluorolastomer, or neoprene, such material being substantially nonconductive of electrical current, comfortable, and readily cleanable. Alternatively, flexible ring 22 may be fabricated from an elastomeric material that is made conductive by, for example, embedding carbon particles in the elastomeric material during fabrication. Flexible ring 22 is flexible so that ring 22 can adapt to the particular anatomy upon which it will be worn. In particular, flexible ring 22 is configured to fit about the corona 36, demarcating where the glans 38 and the shaft 40 of a penis 42 join.

Electrically conductive section 24 is desirably fabricated from an elastomeric material such as silicone, fluorolastomer, or neoprene for comfort and cleanability. Electrically conductive section 24 is made conductive along the length of section 24 by embedding carbon particles in the elastomeric material during fabrication. Alternatively, electrically conductive section 24 may be fabricated from other pliable conductive materials such as conductive ceramic, metals, twisted or braided wires, and such.

Hole 32 is sized to allow intermediate portion 30 of electrically conductive section 24 to slide within hole 32 as indicated by a bidirectional arrow 44. In addition, electrically conductive section 24 is flexible so that section 24 can adapt to the particular anatomy upon which it will be worn. In particular, a region 46 of electrically conductive section 24 between first end 26 and intermediate portion 30 is configured to fit over and contact glans 38 and the urethral opening (not shown) of penis 42.

Electrode apparatus 20 further includes a nonconductive washer 48, a conductive tube 50, a nonconductive sheath 52, and an O-ring 54 installed over the end of electrical contact 34. With particular reference to FIG. 2, during assembly second end 28 of electrically conductive section 24 is directed through hole 32 of flexible ring 22. Washer 48 is threaded onto second end 24 and second end 24 is plugged directly into a first tube end 56 of conductive tube 50. Conductive tube 50 is then inserted into nonconductive sheath 52, and a plug end 58 of electrical contact 34 is plugged into a second tube end 60 of conductive tube 50. Tube 50 is fabricated from an elastomeric material and made conductive by embedded carbon particles so that tube 50 forms a path for electrical communication between electrical contact 34 and electrically conductive section 24.

Electrode apparatus 20 is readily assembled and disassembled without the use of tools. In addition, the simplicity of the coupling between the components allows electrode apparatus 20 to be easily disassembled for cleaning and replacement of parts.

With particular reference to FIG. 3, following assembly, electricity is conducted to electrically conductive section 24 through conductive tube 52 when electrical contact 34 is connected to a source of electricity, typically a controller allowing for adjustment of current (not shown). The controller will typically include a jack 62 and a wire 64 connected to jack 62. Wire 64 will typically terminate with a first connector 66 configured for attachment to electrical contact 34 and a second connector 68 connected to the body, for example, on the band surrounding shaft 40, for completing the electrical path through penis 42.

Electrode apparatus 20 is configured by placing flexible ring 22 about corona 36. Electrically conductive section 24 is then adjusted in size by either pushing or pulling section 24 through hole 32 of flexible ring 22 until section 24 contacts glans 38 and the urethral opening. In this configuration, electrode apparatus 20 is particularly effective for causing erection or orgasm when electricity is applied at electrical contact 34. Furthermore, electrode apparatus may be comfortably worn on the penis from rest through engorgement since electrically conductive section 24 is readily adjusted and ring 22 is fabricated from flexible material.

As discussed previously, flexible ring 22 may be either electrically conductive or nonconductive. When flexible ring 22 is made electrically conductive, ring 22 is in electrical communication with electrically conductive section 24 so that electricity is applied to both corona 36 and glans 38 of penis 42. Alternatively, when flexible ring 22 is made electrically nonconductive, electricity is applied only to glans 38. As such, electrode apparatus 20 is readily adaptable to suit the needs of the user.

Figure 4:
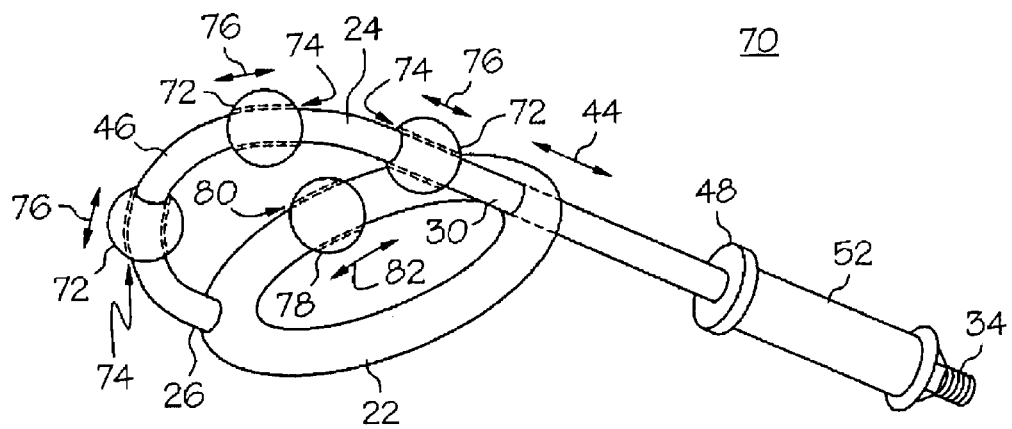
FIG. 4 shows a perspective view of an alternative electrode apparatus in accordance with the present invention.

FIG. 4 shows a perspective view of an alternative electrode apparatus 70 in accordance with the present invention. Electrode apparatus 70 includes flexible ring 22, electrically conductive section 24, and electrical contact 34. Apparatus 70 is constructed similarly to electrode apparatus 20. Electrode apparatus 70 further includes conductive spheres 72 coupled to region 46 between first end 26 and intermediate portion 30 of electrically conductive section 24.

Each of conductive spheres 72 includes an interior passage 74 (represented by hidden lines) through which region 46 of electrically conductive section 24 is routed. Interior passage 74 is sized such that conductive spheres 72 are slidable along electrically conductive section 24 as denoted by bidirectional arrows 76. Conductive spheres 72 may be constructed of silicon composite conductive material, conductive ceramic, conductive metals, and so forth that move freely along electrically conductive section 24.

Electrode apparatus 70 may also include one or more conductive spheres 78 coupled to flexible ring 22, of which only one is shown. Like spheres 72, conductive sphere 78 has an interior passage 80 (represented by hidden lines) sized such that conductive sphere 78 is slidable about flexible ring 22 as denoted by a bidirectional arrow 82. Like conductive spheres 72, conductive sphere 78 may be constructed of silicon composite conductive material, conductive ceramic, conductive metals, and so forth that moves freely along flexible ring 22.

Conductive spheres 72 are in electrical communication with electrically conductive section 24. Conductive spheres 78 are utilized when flexible ring 22 is made conductive, so that conductive spheres 78 are in electrical communication with flexible ring 22. Conductive spheres 72 and 78 are utilized to impart concentrated, or focused, electrical energy to particular regions on corona 36 (FIG. 3) and/or glans 38 (FIG. 3) of penis 42 (FIG. 3). That is, the user may position spheres 72 and 78 to an appropriate location best suited to the needs of the user.

Electrode apparatus 70 is shown having both conductive spheres 72 on electrically conductive section 24 and conductive spheres 78 on flexible ring 22. However, it should be understood that electrode apparatus 70 may be configured to include only spheres 72 or alternatively spheres 78 as desired by the user.

Figure 5:
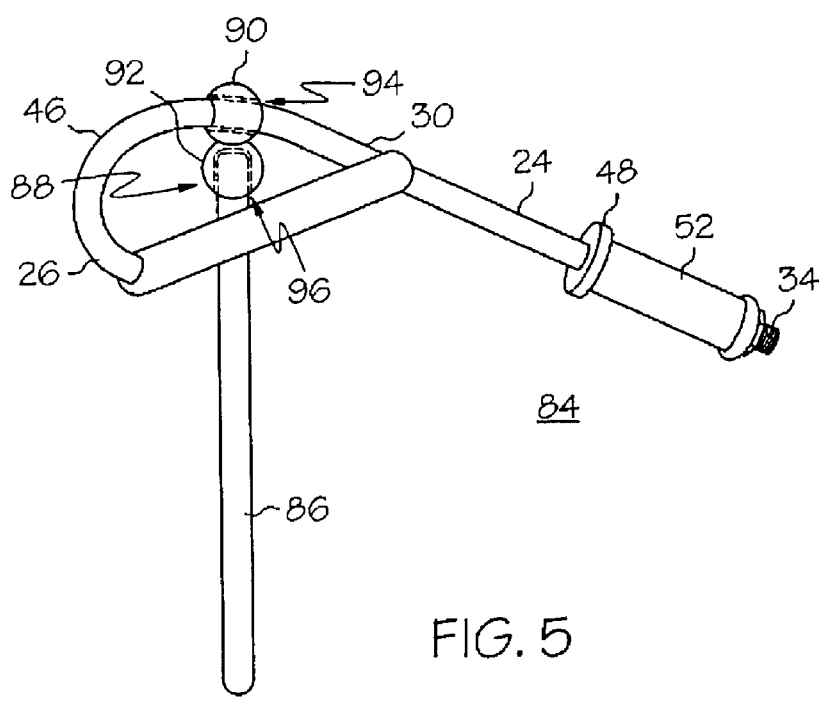
FIG. 5 shows a perspective view of another alternative electrode apparatus in accordance with the present invention.

FIG. 5 shows a perspective view of another alternative electrode apparatus 84 in accordance with the present invention. Electrode apparatus 84 includes flexible ring 22, electrically conductive section 24, and electrical contact 34 and is constructed similarly to electrode apparatus 20. Electrode apparatus 70 further includes a second electrically conductive section 86 extending from region 46 between first end 26 and intermediate portion 30 of section 24.

Conductive section 86 has a proximal end 88 slidably attached to region 46 through a first conductive sphere 90 and a second conductive sphere 92. In particular, first conductive sphere 90 includes an interior passage 94 through which region 46 of electrically conductive section 24 is routed, as denoted by dashed lines. Second sphere 92 is bonded to first sphere 90, and proximal end 88 of second electrically conductive section 86 is inserted by press-fitting into an interior passage 96 of second sphere 90, as denoted by dashed lines.

First and second electrically conductive spheres 90 and 92, respectively, and second electrically conductive section 86 are in electrical communication with electrically conductive section 24. Conductive spheres 90 and 92 and are utilized to impart concentrated, or focused, electrical energy to the urethral opening of penis 42 (FIG. 3). In addition, second electrically conductive section 86 is utilized to impart concentrated electrical energy within the urethra. Second electrically conductive section 86 may be readily removed from second sphere 92 for cleaning. Likewise, conductive sphere 90 may be readily removed from electrically conductive section 24 by disassembling electrode apparatus 84 in a manner similar to the assembly process shown and described in connection with electrode apparatus 20 (FIG. 2).

Figure 6:
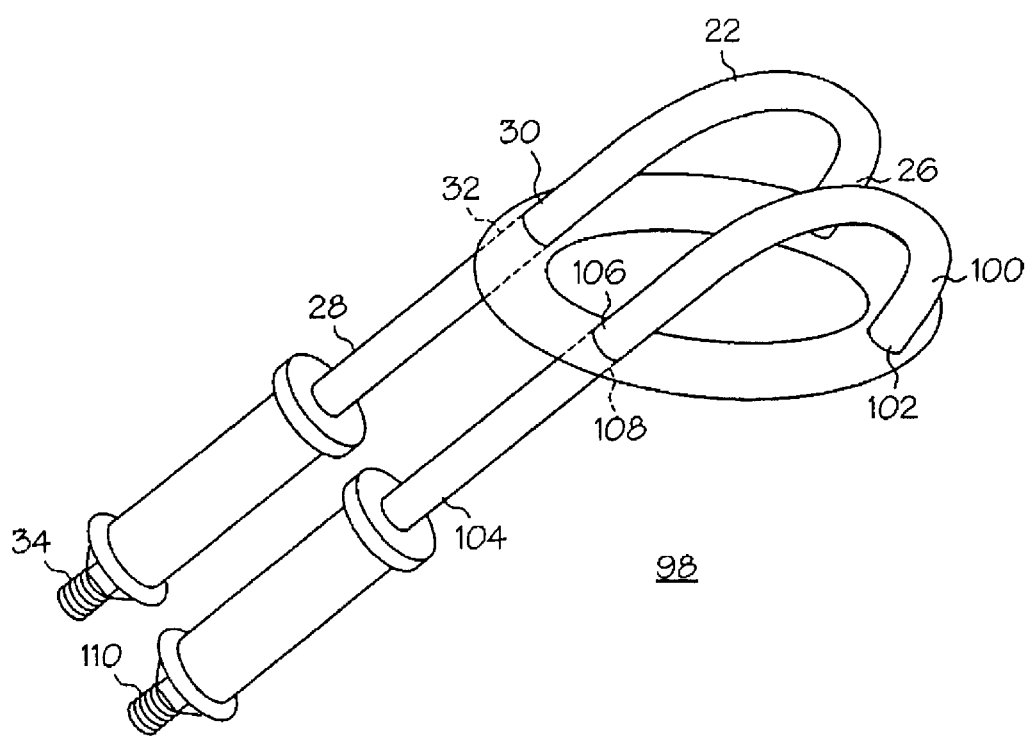
FIG. 6 shows a perspective view of yet another alternative electrode apparatus in accordance with the present invention.

FIG. 6 shows a perspective view of yet another alternative electrode apparatus 98 in accordance with the present invention. Electrode apparatus 98 includes flexible ring 22, electrically conductive section 24, and electrical contact 34. Electrode apparatus 98 further includes a second electrically conductive section 100. Second electrically conductive section 100 has a third end 102, a fourth end 104, and a second intermediate portion 106 between third and fourth ends 102 and 104, respectively. Like the construction of electrically conductive section 24, third end 102 is coupled to and extends from flexible ring 22 and second intermediate portion 106 extends through a second hole 108 extending through flexible ring 22 as denoted by dashed lines.

Electrode apparatus 98 is positioned by placing flexible ring 22 about corona 36 (FIG. 3). Electrically conductive sections 24 and 100 may then be positioned to contact glans 38 (FIG. 3) as desired by the user. A second electrical contact 110 is in electrical communication with fourth end 104. In this configuration, electrode apparatus 98 includes two electrical contacts, i.e., first and second electrical contacts 34 and 110, for connection to first and second connectors 66 and 68, respectively (FIG. 3), from a controller (not shown). In this manner, the desired electrical energy may be imparted on glans 38 (FIG. 3).

In an alternate embodiment, first contact 34 and second contact 110 may be combined at an electrical junction to form a single electrical contact for connection to the controller (not shown). Accordingly, first connector 66 (FIG. 3) may be connected to the single electrical contact to supply electrical energy to both electrically conductive sections 24 and 100. In addition, second connector 68 may be connected to another point on the body for example on the band surrounding penis 42 to complete the electrical path through penis 42, as shown in FIG. 3.

In summary, the present invention teaches an electrode apparatus for the electrical stimulation of the penile glans, corona, and urethral tissue to induce erection and/or orgasm. Furthermore, an electrode apparatus is provided that includes a flexible ring and adjustable electrically conductive sections for securely and comfortably retaining the device on penile tissue before and during penile engorgement. Furthermore, the electrode apparatus and its various embodiments are readily assembled and disassembled for cleaning, replacement of components, and reconfiguration.

Although the preferred embodiments of the invention have been illustrated and described in detail, it will be readily apparent to those skilled in the art that various modifications may be made therein without departing from the spirit of the invention or from the scope of the appended claims.

What is claimed is:

1. An electrode apparatus comprising:
   a flexible ring;
   an electrically conductive section having a first end, a second end, and an intermediate portion between said first and second ends, said first end coupled to and extending from said flexible ring, and said intermediate portion extending through a hole in said flexible ring; and
   an electrical contact in electrical communication with said second end.

2. An electrode apparatus as claimed in claim 1 wherein said flexible ring is electrically conductive and in electrical communication with said electrically conductive section.

3. An electrode apparatus as claimed in claim 2 further comprising an electrically conductive sphere coupled to said flexible ring.

4. An electrode apparatus as claimed in claim 3 wherein said electrically conductive sphere is a first electrically conductive sphere, and said apparatus further comprises a second electrically conductive sphere coupled to a region of said electrically conductive section between said first end and said intermediate portion.

5. An electrode apparatus as claimed in claim 1 wherein said flexible ring is substantially nonconductive of electrical current.

6. An electrode apparatus as claimed in claim 1 wherein said electrically conductive section is conductive along a length of said section.

7. An electrode apparatus as claimed in claim 1 wherein said hole is sized to allow said intermediate portion of said electrically conductive section to slide within said hole.

8. An electrode apparatus as claimed in claim 1 further comprising an electrically conductive sphere coupled to a region of said electrically conductive section between said first end and said intermediate portion.

9. An electrode apparatus as claimed in claim 8 wherein said electrically conductive sphere includes an interior passage through which said region of said electrically conductive section is routed, said sphere being slidable along said electrically conductive section.

10. An electrode apparatus as claimed in claim 1 wherein said electrically conductive section is a first section, and said apparatus further comprises a second electrically conductive section having a third end, a fourth end, and a second intermediate portion between said third and fourth ends, said third end coupled to and extending from said flexible ring, and said second intermediate portion extending through a second hole in said flexible ring.

11. An electrode apparatus as claimed in claim 1 wherein said electrically conductive section is a first section, and said apparatus further comprises a second electrically conductive section extending from a region of said first section between said first end and said intermediate portion, said second section being in electrical communication with said first section.

12. An electrode apparatus as claimed in claim 11 wherein said second electrically conductive section is slidably coupled to said first section.

13. An electrode apparatus as claimed in claim 11 wherein a proximal end of said second section is coupled to said first section, and said apparatus further comprises a conductive sphere coupled to said proximal end of said second section.

14. An electrode apparatus comprising:
   a flexible ring;
   an electrically conductive section having a first end, a second end, and an intermediate portion between said first and second ends, said first end coupled to and extending from said flexible ring, and said intermediate portion extending through a hole in said flexible ring, said hole being sized to allow said intermediate portion of said electrically conductive section to slide within said hole;
   an electrically conductive sphere coupled to and in electrical communication with said electrically conductive section in a region of said section between said first end and said intermediate portion; and
   an electrical contact in electrical communication with said second end.

15. An electrode apparatus as claimed in claim 14 wherein said electrically conductive sphere includes an interior passage through which said region of said electrically conductive section is routed, said sphere being slidable along said electrically conductive section.

16. An electrode apparatus as claimed in claim 14 wherein:
   said flexible ring is electrically conductive and in electrical communication with said electrically conductive section; and
   said apparatus further comprises an electrically conductive sphere coupled to said flexible ring.

17. An electrode apparatus as claimed in claim 14 wherein said flexible ring is substantially nonconductive of electrical current.

18. An electrode apparatus comprising:
   a flexible ring;
   a first electrically conductive section having a first end, a second end, and an intermediate portion between said first and second ends, said first end coupled to and extending from said flexible ring, and said intermediate portion extending through a hole in said flexible ring, said hole being sized to allow said intermediate portion of said electrically conductive section to slide within said hole;
   an electrical contact in electrical communication with said second end; and
   a second electrically conductive section extending from said first electrically conductive section in a region of said first section between said first end and said intermediate portion, said second section being in electrical communication with said first section.

19. An electrode apparatus as claimed in claim 18 wherein said second electrically conductive section is slidably coupled to said first section.

20. An electrode apparatus as claimed in claim 18 wherein a proximal end of said second section is coupled to said first section, and said apparatus further comprises a conductive sphere coupled to said proximal end of said second section.

* * * * *